United States Patent [19]

Konishi et al.

[11] Patent Number: 5,082,663

[45] Date of Patent: Jan. 21, 1992

[54] EXTERNAL ADHESIVE PREPARATION CONTAINING STEROIDS

[75] Inventors: Ryoji Konishi; Akihito Oji; Toshikuni Kawaji; Osami Makaya; Manabu Ishihara, all of Kagawa; Akira Iwasa, Yotsukaido, all of Japan

[73] Assignees: Teikoku Seiyaky Co., Ltd., Toyko, Japan; SS Pharmaceutical Co., Ltd., Tokyo, Japan

[21] Appl. No.: 639,758

[22] PCT Filed: Aug. 20, 1987

[86] PCT No.: PCT/JP87/00618

§ 371 Date: Apr. 20, 1988

§ 102(e) Date: Apr. 20, 1988

[87] PCT Pub. No.: WO88/01170

PCT Pub. Date: Feb. 25, 1988

Related U.S. Application Data

[63] Continuation of Ser. No. 189,313, Apr. 20, 1988, abandoned.

[30] Foreign Application Priority Data

Aug. 20, 1986 [JP] Japan .............................. 64-195935
Aug. 20, 1986 [JP] Japan .............................. 64-195936

[51] Int. Cl.$^5$ .................. A61L 15/16; A61L 15/22; A61K 31/56; A61K 31/74

[52] U.S. Cl. .................................. 424/445; 424/456; 424/484; 424/485; 424/486; 424/443; 514/861; 514/863; 514/781; 514/179; 514/182; 514/772.6; 514/772.4

[58] Field of Search .............. 424/484, 485, 486, 445, 424/456, 78, 443; 514/861, 863, 781, 179, 182

[56] References Cited

U.S. PATENT DOCUMENTS 3,928,261  12/1975  Ashidaga et al.
4,008,321  2/1977   Kamishita et al.
4,755,983  8/1988   Takayanagi et al. ............... 424/435

FOREIGN PATENT DOCUMENTS 0072251  8/1981   European Pat. Off.
0161681  11/1985  European Pat. Off.
229393   5/1974   France.
57-50914 3/1982   Japan.

OTHER PUBLICATIONS

Patent Abstracts of Japan, vol. 9, No. 28 (C-264) (1751) Feb. 6, 1985.

Primary Examiner—F. T. Moezie
Attorney, Agent, or Firm—Birch, Stewart, Kolasch & Birch

[57] ABSTRACT

An external adhesive preparation comprising a steroid for treatment of skin diseases in admixture with an adhesive gel base comprising as essential components a water-soluble high molecular weight compound, water and a water-retaining agent. The external adhesive preparation is useful for treatment of skin diseases by applying the preparation spread on a soft support directly to diseased parts on the skin, thereby administering the contained steroid to the skin.

7 Claims, 1 Drawing Sheet

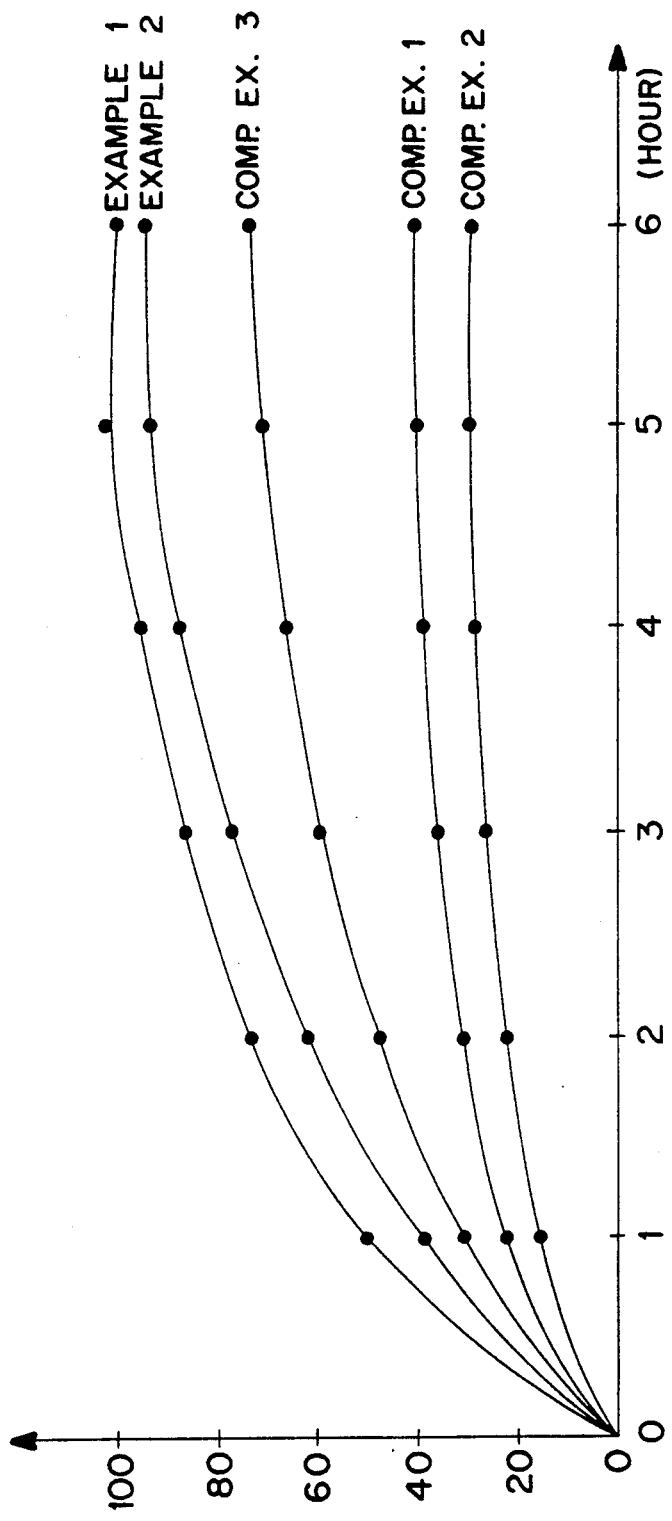

EXTERNAL ADHESIVE PREPARATION CONTAINING STEROIDS

This application is a continuation of application Ser. No. 07/189,313 filed on Apr. 20, 1988, now abandoned.

TECHNICAL FIELD OF THE INVENTION

The present invention relates to an external adhesive preparation containing steroids. More specifically, the present invention relates to an external adhesive preparation containing steroids which is obtained by incorporating a steroid useful for the treatment of skin diseases into an adhesive gel base comprising as essential components a water-soluble high molecular weight compound, water and a water-retaining agent and spreading the resulting composition onto a soft support, said preparation being directly applied to diseased parts on the skin so that the contained steroids are administered to the skin for treatment of the diseases.

PRIOR ART

Hitherto, for the treatment of allergic skin diseases such as eczema, hives, children's strophulus, contoured exudative erythema, Behcet's syndrome, keratodermia palmaris, psoriasis and the like, there have been used oral preparations, injections, external preparations and the like containing cortisone etc. as an active component.

However, these preparations have some side effect or inconvenience in usage. For example, in case of oral preparations, there is a fear of forgetting taking or an excess administration. In case of injections, patients suffer from pain or stress when administering drugs and further it is difficult to be administered by the patients themselves. External preparations such as ointments or lotions not only stain clothes and the like but also are hardly administered in a fixed-amount. Further, in case of external preparations, patients are forced to be given by a physical stimulus to the diseased parts which are most accompanied with urtication and this stimulus sometimes makes worse symptoms. Therefore, the external preparations are not necessarily suitable. For the purpose of obviating the above-mentioned disadvantages, there have been developed tapes which are produced by incorporating a steroid into a pressure sensitive adhesive comprising a natural gum or a copolymer of acrylic acid ester - acrylic acid. These tapes are more advantageous than conventional external preparations in many respects, i.e. they may have an effect similar to occlusive dressing technique by applying them to diseased parts, and they are more easily handled in such a treatment method. However, the application of these tapes to diseased parts induces occasionally contact dermatitis caused by the adhesive itself, folliculitis caused by bacteria etc. on the skin, or cutaneous inflammation due to stimulus of sweat glands. Furthermore, these tapes are still unsatisfactory in that when these tapes are removed, diseased parts are rather injured or keratin is peeled off, and therefore not only is it difficult to apply them successively, but also symptoms may be made worse.

OBJECT OF THE INVENTION

As a result of the present inventors' intensive study to obviate defects of these tapes and the like, it has been found that an excellent adhesive preparation, without defects as seen in the conventional tapes, could be obtained by incorporating a steroid as the active ingredient into an adhesive base comprising as essential components a water-soluble high molecular weight compound, water and a water-retaining agent, and spreading this base on a soft support, and thus, the present invention has been accomplished. That is, the present invention provides an external adhesive preparation which is prepared by incorporating a steroid into an adhesive gel base comprising as essential components a water-soluble high molecular weight compound, water and a water-retaining agent.

BRIEF EXPLANATION OF THE DRAWING

FIG. 1 is a graph showing a cumulative release rate of active agent as to the adhesive preparations of the present invention prepared in Examples 1 and 2 and tapes prepared in Comparative Examples 1 to 3.

DISCLOSURE OF THE INVENTION

The water-soluble high molecular weight compound employed in the external adhesive preparations of the present invention includes gelatin, agar, alginic acid, mannan, carboxymethylcellulose, methylcellulose, polyvinyl alcohol, polyacrylic acid, gum arabic, and the like, as well as metal salts thereof and cross-linked products thereof with organic or inorganic cross-linking agents, and the like. These water-soluble high molecular weight compounds are employed alone or in combination of two or more thereof depending on properties of other materials used in the adhesive gel base and are mixed with the gel base in an amount of from 0.1 to 30 w/w %, preferably from 0.5 to 15 w/w %.

A water-retaining agent includes polyhydric alcohols such as polyethylene glycol, glycerol, sorbitol, maltitol, propylene glycol and 1,3-butanediol. These are employed alone or in combination of two or more thereof and are mixed with the gel base in an amount of from 5 to 60 w/w %, preferably from 10 to 50 w/w %. Also there may be employed highly absorptive high molecular weight compounds, such as starch - acrylonitrile graft copolymer, starch-acrylic acid graft copolymer, starch - styrenesulfonic acid graft copolymer, starch - vinylsulfonic acid graft copolymer, cellulose - acrylonitrile graft copolymer, cellulose - styrenesulfonic acid graft copolymer, a cross-linked product of carboxymethylcellulose, a cross-linked product of polyvinyl alcohol, a saponification product of acrylic acid - vinyl acetate, a cross-linked product of polyacrylate, a saponification product of polyacrylonitrilic polymer and a cross-linked product of polyethylene glycol diacrylate. These are employed in an amount of from 0.01 to 10.0 w/w %, preferably from 0.05 to 7.0 w/w %.

One of the characteristics of the adhesive gel base employed in the present invention is that it contains water, thereby enhancing an absorption of steroids as an active component. The water content is in the range of from 10 to 70 w/w %, preferably from 20 to 50 w/w %.

The steroids which are an active component of the external adhesive preparations of the present invention include, for example, deprodone propionate, fluocinolone acetonide, triamcinolone acetonide, dexamethasone, methylprednisolone, prednisolone, hydrocortisone, paramethasone, betamethasone, betamethasone sodium phosphate, dexamethasone acetate, cortisone acetate, hydrocortisone acetate, methylprednisolone acetate, clobetasol propionate, hydrocortisone butyrate, fluocinonide, fluorometholone, fludroxycortide, flumethasone pivalate, beclomethasone propionate, betamethasone valerate, methylprednisolone acetate and the like. These steroids- are incorporated into the adhesive gel base in an amount of from 0.001 to 1 w/w %, preferably from 0.005 to 0.5 w/w %, more preferably from 0.01 to 0.25 w/w %.

In order to improve a solubility or a dispersibility of the above steroids in water, the gel base may contain oil components, surfactants and the like such as crotamiton, benzyl alcohol, isopropyl myristate, ethylene glycol, diethyl sebacate-2-ethyl-5-pyrrolidone.

Further, if necessary, known stabilizing agents, antioxidants, pH controlling agents or inorganic fillers may also be added. The stabilizing agents and antioxidants include, for example, disodium edetate, tetrasodium edetate, sodium metabisulfite, dibutylhydroxytoluene (BHT), butylhydroxyanisol (BHA), ascorbic acid, sodium ascorbate, erythorbic acid, sodium erythorbate, sodium sulfite, d-α-tocopherol, tocopherol acetate, guaiacum resin, nordihydroguaiaretic acid, propyl gallate and the like, which may be used alone or in combination of two or more thereof. These are mixed usually in an amount of from 0.005 to 1.0 w/w %, preferably from 0.01 to 0.5 w/w %.

A support employed in the present invention is preferably such a soft one and being able to follow a movement of a human body, and includes various woven fabrics, non-woven fabrics, flannels and the like. The external adhesive preparations of the present invention are expected to have an effect such as that associated with occlusive dressing techniques since the adhesive gel base layer is a continuous phase. However, when more powerful effects than that of occlusive dressing techniques are desired, the above-mentioned support may be laminated by ethylene vinyl acetate, polyethylene, polyvinyl chloride, polyurethane and the like.

The external adhesive preparation of the present invention has less side effects such as cutaneous inflammation and further less injury of diseased parts or peeling off of keratin when the preparations are removed as compared with the conventional tapes, and hence, the present preparation can be used successively. Moreover, when the external adhesive preparation of the present invention is applied to diseased parts on the skin, not only is an effect of occlusive dressing techniques expected, as in the case of conventional tapes, but also more excellent treatment effects can be obtained through increased absorption of the main component steroid, which is induced by an active hydration of the keratin layer owing to water contained in the external adhesive preparation of the present invention.

In order to exhibit the medical effects, by applying the external adhesive preparation to cutaneous diseased parts, it is necessary that the active ingredient is released from the base and transferred into the cutaneous diseased part. It is known that an affinity between the active ingredient and the base is related to the above and has an influence on the medical effects. The affinity is influenced by various factors such as the solubility, the diffusion coefficient, and the thermodynamic activity, and the like of the base or active agent in the base. In case of the external adhesive preparation of the present invention, these factors are controllable by varying a combination of the base components thus enabling one to adjust an optimum concentration of each active ingredient, and thereby, desired treatment effects can be more effectively exhibited as compared with the other conventional preparations.

THE BEST MODE FOR WORKING THE INVENTION

The present invention is more specifically illustrated by the following Examples and Experiments. In the Examples, "part" means a part by weight.

Example 1

A mixture of 31 parts of water, 5.0 parts of gelatin, 0.1 part of methyl p-hydroxybenzoate, 0.2 part of citric acid, 0.2 part of deprodone propionate, 1.0 part of crotamiton, 20 parts of sorbitol, 30 parts of glycerol and 4.0 parts of polyacrylic acid is stirred with heating in a kneader to give a solution, and thereto is added a solution of 0.5 part of aluminum potassium sulfate in 8 parts of water, and the mixture is stirred well to give an adhesive gel base. This adhesive gel base is applied and spread on a release paper in an amount of 200 g/m² in a conventional manner, and then transferred to polyurethane-laminated non-woven fabric made of rayon, which is cut in a desired size to give an external adhesive preparation containing 40 μg/cm² of deprodone propionate.

Example 2

A mixture of 25 parts of water, 10 parts of polyacrylic acid, 5 parts of zinc white, 6 parts of polyvinyl alcohol, 3.0 parts of benzyl alcohol, 0.2 part of deprodone propionate, 0.1 part of propyl p-hydroxybenzoate, 8.0 parts of carboxymethylcellulose sodium, 20 parts of glycerol and 20 parts of sorbitol is dissolved in a kneader in the same manner as in Example 1, and thereto is added a solution of 0.2 part of dihydroxyaluminum aminoacetate in 2.5 parts of water, and the mixture is well stirred to give an adhesive gel base. Using this base, the procedure of Example 1 is repeated to give an external adhesive preparation containing 40 μg/cm² of deprodone propionate.

Example 3

Except that 0.025 part of deprodone propionate is employed, the procedure of Example 1 is repeated to give an external adhesive preparation containing 5 μg/cm² of deprodone propionate.

Example 4

Except that 0.05 part of deprodone propionate is employed, the procedure of Example 1 is repeated to give an external adhesive preparation containing 10 μg/cm² of deprodone propionate.

Example 5

Except that 0.1 part of deprodone propionate is employed, the procedure of Example 1 is repeated to give an external adhesive preparation containing 20 μg/cm² of deprodone propionate.

Example 6

Except that 0.4 part of deprodone propionate is employed, the procedure of Example 1 is repeated to give an external adhesive preparation containing 80 μg/cm² of deprodone propionate.

Comparative Example 1

A four-necked flask is charged with a mixture of 7.0 parts of acrylic acid, 68 parts of 2-ethylhexyl acrylate, 25 parts of vinyl acetate, 0.2 part of azobisisobutyronitrile and 150 parts of ethyl acetate under nitrogen. The mixture is stirred with heating at 65° C.–70° C. to conduct polymerization to give an acrylic adhesive agent having 40% of a solid content. To 99.6 parts (in solid content) of the adhesive agent is added 0.4 part of deprodone propionate, and the mixture is applied to in an amount of 100 g/m² (in dry state) in a conventional manner, which is laminated on polyethylene film to give an acrylic adhesive tape containing 40 μg/cm² of deprodone propionate.

Comparative Example 2

Fifty parts of raw rubber is dissolved in 203 parts of toluene and therein are dissolved with stirring 10 parts of polybutene, 38 parts of ester gum and 2.0 parts of dibutylhydroxytoluene to give a natural gum adhesive agent having 33% of a solid content. Then, after 0.4 part of deprodone propionate is added to 99.6 parts (in solid content) of the adhesive agent, the procedure of Comparative Example 1 is repeated to give a natural gum adhesive tape containing 40 μg/cm² of deprodone propionate.

Comparative Example 3

A mixture of 29 parts of styrene-isoprene-styrene copolymer, 47 parts of an alicyclic saturated hydrocarbon petroleum resin, 10 parts of a liquid polyisoprene rubber, 12.6 parts of a liquid paraffin and 1.0 part of an antioxidant is dissolved with heating at 160° C. in a kneader. After stirring, the mixture is cooled to 120° C. and thereto is added 0.4 part of deprodone propionate, and the mixture is applied to a release paper with a coator in an amount of 100 g/m². After cooling, the mixture is transferred to a polyethylene vinyl acetate film, which is cut in a desired size to give a hot-melt type adhesive tape containing 40 μg/cm² of deprodone propionate.

Experiment 1

The vasoconstrictor test was carried out as to the adhesive preparations prepared in Examples 1–6, the tapes prepared in Comparative Examples 1–3, a commercially available acrylic adhesive tape containing 4 μg/cm² of fludroxycortide and a commercially available acrylic adhesive tape containing 8 μg/cm² of fluocinolone acetonide to compare effects of these preparations or tapes.

These adhesive preparations and tapes containing steroids, and further, blank adhesive preparations and tapes which were prepared by removing deprodone propionate from the adhesive preparations in Examples 1–2 and the tapes in Comparative Examples 1–3 (hereinafter, referred to merely as blank of Example 1 and the like) were punched in a circular form of 15 mm diameter to give test samples. The samples were adhered to backs of 20 healthy adult men. Application periods were 30 minutes, 1 hour, 2 hours and 4 hours. After removal, the applied portions were wiped with slightly warm water. Two hours later a degree of the vasoconstrictor activity was evaluated. The experiment was carried out by a double blind test.

The results are shown in Table 1. The figures in the table are % of a number having the vasoconstrictor activity in the 20 volunteers.

TABLE 1

| Sample name | Vasoconstrictor test | | | |
|---|---|---|---|---|
| | 30 min. application | 1 hour application | 2 hours application | 4 hours application |
| Example 1 | 75 | 85 | 100 | 100 |
| Example 2 | 60 | 90 | 95 | 100 |
| Example 3 | 5 | 15 | 50 | 55 |
| Example 4 | 10 | 30 | 65 | 80 |
| Example 5 | 30 | 55 | 75 | 100 |
| Example 6 | 95 | 100 | 100 | 100 |
| Comp. Ex. 1 | 10 | 55 | 70 | 90 |
| Comp. Ex. 2 | 15 | 50 | 75 | 90 |
| Comp. Ex. 3 | 30 | 60 | 85 | 100 |
| Commercial product 1 | 5 | 25 | 55 | 60 |
| Commercial product 2 | 5 | 15 | 40 | 65 |
| Example 1 | 5 | 5 | 0 | 5 |
| Example 2 | 5 | 0 | 5 | 5 |
| Comp. Ex. 1 | 0 | 5 | 0 | 0 |
| Comp. Ex. 2 | 0 | 0 | 0 | 0 |
| Comp. Ex. 3 | 0 | 0 | 5 | 0 |

Experiment 2

Employing Franz Diffusion Cell (manufactured by CROWN GLASS Co. Inc.), active agent release patterns of each adhesive preparation and tape were evaluated. The test samples were punched into 15 mm diameter and adhered to silicone membrane and the amount of deprodone propionate transferred into phosphate buffer of pH 7.4 was measured by HPLC. The measurement was carried out over a period of 6 hours at an interval of 1 hour. A released amount of the active agent was calculated based on the charged amount of the active agent and a cumulative release rate (%) (the release amount/the charged amount ×100) was shown in graph (FIG. 1).

Experiment 3

In the case of the sample adhered for 4 hours in Experiment 1, conditions of cutaneous stimulus were observed immediately, 24 hours and 48 hours after peeling off the sample, and evaluated as 0: no reaction, 0.5: slight erythema, 1: erythema, 2: erythema with edema, 3: small blister, 4: large blister. A mean strength of cutaneous stimulus was calculated by multiplying these figures with a number showing these conditions, which is then divided by a total number of volunteers. The results are shown in Table 2.

TABLE 2

| Sample name | Strength of cutaneous stimulus | | |
|---|---|---|---|
| | immed. after removal | 24 hours after removal | 48 hours after removal |
| Example 1 | 0.075 | 0.100 | 0 |
| Example 2 | 0.100 | 0.075 | 0 |
| Example 3 | 0.225 | 0.100 | 0.075 |
| Example 4 | 0.150 | 0.100 | 0 |
| Example 5 | 0.075 | 0.05 | 0 |
| Example 6 | 0.05 | 0.075 | 0 |
| Comp. Example 1 | 0.25 | 0.125 | 0.050 |
| Comp. Example 2 | 0.200 | 0.200 | 0.075 |
| Comp. Example 3 | 0.175 | 0.125 | 0.075 |
| Commercial product 1 | 0.600 | 0.200 | 0.150 |
| Commercial product 2 | 0.525 | 0.225 | 0.100 |
| Example 1 | 0.200 | 0.100 | 0.050 |
| Example 2 | 0.325 | 0.100 | 0.025 |
| Comp. Ex. 1 | 0.500 | 0.200 | 0.050 |
| Comp. Ex. 2 | 0.575 | 0.100 | 0.025 |

TABLE 2-continued

| Sample name | Strength of cutaneous stimulus | | |
|---|---|---|---|
| | immed. after removal | 24 hours after removal | 48 hours after removal |
| Comp. Ex. 3 | 0.375 | 0.150 | 0.025 |

Example 7

A mixture of 31 parts of water, 5.0 parts of gelatin, 0.1 part of methyl p-hydroxybenzoate, 0.2 part of citric acid, 0.1 part of triamcinolone acetonide, 1.0 part of crotamiton, 20 parts of sorbitol, 30 parts of glycerol and 4.0 parts of polyacrylic acid is stirred with heating in a kneader to give a solution, and thereto is added a solution of 0.5 part of aluminum potassium sulfate in 8 parts of water, and the mixture is stirred well to give an adhesive gel base. This adhesive gel base is applied and spread on a release paper in an amount of 200 g/m$^2$ in a conventional manner, and then transferred to a polyurethanelaminated non-woven fabric made of rayon, which is cut in a desired size to give an external adhesive preparation containing 20 μg/cm$^2$ of triamcinolone acetonide.

Example 8

A mixture of 25 parts of water, 10 parts of polyacrylic acid, 5 parts of zinc white, 6 parts of polyvinyl alcohol, 3.0 parts of benzyl alcohol, 1.0 part of hydrocortisone, 0.1 part of propyl p-hydroxybenzoate, 8.0 parts of carboxymethylcellulose sodium, 20 parts of glycerol and 20 parts of sorbitol is dissolved in a kneader in the same manner as in Example 7, and thereto is added a solution of 0.2 part of dihydroxyaluminum aminoacetate in 2.5 parts of water, and the mixture is well stirred to give an adhesive gel base. Using this base, the procedure of Example 7 is repeated to give an external adhesive preparation containing 200 μg/cm$^2$ of hydrocortisone.

Example 9

Except that 0.1 part of dexamethasone acetate is employed, the procedure of Example 7 is repeated to give an external adhesive preparation containing 20 μg/cm$^2$ of dexamethasone acetate.

Example 10

Except that 0.25 part of methylprednisolone is employed, the procedure of Example 7 is repeated to give an external adhesive preparation containing 50 μg/cm$^2$ of methylprednisolone.

Example 11

Except that 0.5 part of prednisolone is employed, the procedure of Example 7 is repeated to give an external adhesive preparation containing 100 μg/cm$^2$ of prednisolone.

Example 12

Except that 0.04 part of fluocinolone acetonide is employed, the procedure of Example 7 is repeated to give an external adhesive preparation containing 8 μg/cm$^2$ of fluocinolone acetonide.

Experiment 4

The vasoconstrictor test was carried out as to the adhesive preparations prepared in Examples 7-12, commercially available acrylic adhesive tapes containing 4 μg/cm$^2$ of fludroxycortide, 8 μg/cm$^2$ of fluocinolone acetonide and 6 μg/cm$^2$ of betamethasone valerate, respectively, to compare effects of these preparations or tapes. These adhesive preparations and the commercially available tapes containing steroids were punched in a circular form of 10 mm diameter to give test samples. The samples were randomly assigned to and adhered to middle backs of 10 healthy adult men. Application periods were 30 minutes, 1 hour, 2 hours and 4 hours. The vasoconstrictor activity was evaluated 2 hours and 4 hours after removal.

The results are shown in Tables 3-6. Table 3 and Table 4 show the results of vasoconstrictor activity when evaluated 2 hours after removal, wherein Table 3 shows a number of positive and Table 4 shows a number of pseudpositive or positive in 10 persons tested. Table 5 and Table 6 show the results when evaluated 4 hours after removal wherein Table 5 shows a number of positive and Table 6 shows a number of pseud-positive or positive in 10 persons tested.

TABLE 3

| Sample name | Active ingredient | | Application period (h) | | | |
|---|---|---|---|---|---|---|
| | Name | conc. (μg/cm$^2$) | 0.5 | 1.0 | 2.0 | 4.0 |
| Ex. 12 | Fluocinolone acetonide | 8 | 0 | 0 | 3 | 7 |
| Ex. 7 | Triamcinolone acetonide | 20 | 0 | 3 | 5 | 7 |
| Ex. 9 | Dexamethasone acetate | 20 | 0 | 1 | 4 | 6 |
| Ex. 10 | Methylprednisolone | 50 | 0 | 0 | 0 | 5 |
| Ex. 11 | Prednisolone | 100 | 0 | 0 | 1 | 5 |
| Ex. 8 | Hydrocortisone | 200 | 0 | 0 | 1 | 0 |
| Commerc. product 1 | Fludroxycortide | 4 | 0 | 0 | 2 | 4 |
| Commerc. product 2 | Fluocinolone acetonide | 8 | 0 | 0 | 0 | 2 |
| Commerc. product 3 | Betamethasone valerate | 6 | 0 | 0 | 1 | 4 |

TABLE 4

| Sample name | Active ingredient | | Application period (h) | | | |
|---|---|---|---|---|---|---|
| | Name | conc. (μg/cm$^2$) | 0.5 | 1.0 | 2.0 | 4.0 |
| Ex. 12 | Fluocinolone acetonide | 8 | 0 | 1 | 5 | 9 |
| Ex. 7 | Triamcinolone acetonide | 20 | 1 | 6 | 9 | 9 |
| Ex. 9 | Dexamethasone acetate | 20 | 1 | 4 | 6 | 10 |
| Ex. 10 | Methylprednisolone | 50 | 0 | 1 | 6 | 6 |
| Ex. 11 | Prednisolone | 100 | 1 | 1 | 3 | 5 |
| Ex. 8 | Hydrocortisone | 200 | 1 | 0 | 2 | 6 |
| Commerc. product 1 | Fludroxycortide | 4 | 0 | 2 | 4 | 10 |
| Commerc. product 2 | Fluocinolone acetonide | 8 | 0 | 3 | 2 | 6 |
| Commerc. product 3 | Betamethasone valerate | 6 | 1 | 2 | 6 | 8 |

TABLE 5

| Sample name | Active ingredient | | Application period (h) | | | |
|---|---|---|---|---|---|---|
| | Name | conc. (μg/cm$^2$) | 0.5 | 1.0 | 2.0 | 4.0 |
| Ex. 12 | Fluocinolone acetonide | 8 | 0 | 1 | 7 | 10 |
| Ex. 7 | Triamcinolone acetonide | 20 | 1 | 5 | 8 | 9 |
| Ex. 9 | Dexamethasone acetate | 20 | 0 | 5 | 8 | 10 |

TABLE 5-continued

| Sample name | Active ingredient Name | conc. (μg/cm²) | Application period (h) 0.5 | 1.0 | 2.0 | 4.0 |
|---|---|---|---|---|---|---|
| Ex. 10 | Methyl-prednisolone | 50 | 0 | 1 | 2 | 7 |
| Ex. 11 | Prednisolone | 100 | 0 | 0 | 1 | 3 |
| Ex. 8 | Hydrocortisone | 200 | 0 | 0 | 2 | 2 |
| Commerc. product 1 | Fludroxycortide | 4 | 0 | 0 | 3 | 7 |
| Commerc. product 2 | Fluocinolone acetonide | 8 | 0 | 0 | 1 | 6 |
| Commerc. product 3 | Betamethasone valerate | 6 | 0 | 0 | 7 | 9 |

TABLE 6

| Sample name | Active ingredient Name | conc. (μg/cm²) | Application period (h) 0.5 | 1.0 | 2.0 | 4.0 |
|---|---|---|---|---|---|---|
| Ex. 12 | Fluocinolone acetonide | 8 | 2 | 6 | 8 | 10 |
| Ex. 7 | Triamcinolone acetonide | 20 | 4 | 8 | 9 | 10 |
| Ex. 9 | Dexamethasone acetate | 20 | 3 | 9 | 9 | 10 |
| Ex. 10 | Methyl-prednisolone | 50 | 0 | 1 | 5 | 9 |
| Ex. 11 | Prednisolone | 100 | 1 | 3 | 4 | 9 |
| Ex. 8 | Hydrocortisone | 200 | 0 | 0 | 6 | 5 |
| Commerc. product 1 | Fludroxycortide | 4 | 2 | 1 | 6 | 9 |
| Commerc. product 2 | Fluocinolone acetonide | 8 | 0 | 2 | 3 | 9 |
| Commerc. product 3 | Betamethasone valerate | 6 | 0 | 3 | 7 | 9 |

Example 13

A mixture of 35 parts of water, 1.5 part of gelatin, 1 part of urea, 0.5 part of methyl benzoate, 0.25 part of d-tartaric acid, 6 parts of polyacrylic acid, 1 part of hydrocortisone, 0.1 part of d-α-tocopherol, 14 parts of sorbitol, 1 part of crotamiton, 10 parts of glycerol, 3 parts of carboxymethylcellulose sodium and 4 parts of sodium polyacrylate is stirred in a kneader with heating to give a solution, and thereto are added 0.55 part of dihydroxyaluminum aminoacetate and 0.15 part of ascorbic acid, and further water is added so as to make a total volume of 100 parts, followed by stirring the mixture well to give an adhesive gel. Using this base, the procedure of Example 1 is repeated to give an external adhesive preparation containing 200 μg/cm² of hydrocortisone.

Example 14

Except that 0.08 part of tetrasodium edetate and 0.1 part of dexamethasone acetate are employed, the procedure of Example 13 is repeated to give an external adhesive preparation containing dexamethasone acetate.

Example 15

Except that 0.04 part of disodium edetate, 0.15 part of sodium ascorbate and 0.25 part of Methylprednisolone, the procedure of Example 13 is repeated to give an external adhesive preparation containing methylprednisolone.

Example 16

Except that 0.25 part of prednisolone and 0.15 part of erythorbic acid, the procedure of Example 13 is repeated to give an external adhesive preparation containing prednisolone.

Example 17

Except that 0.04 part of fluocinolone acetonide, 0.05 part of disodium edetate and 0.1 part of BHT, the procedure of Example 13 is repeated to give an external adhesive preparation containing fluocinolone acetonide.

Example 18

Except that 0.1 part of triamcinolone acetonide, 0.05 part of disodium edetate and 0.1 part of sodium metabisulfite, the procedure of Example 13 is repeated to give an external adhesive preparation containing triamcinolone acetonide.

We claim:

1. An external adhesive preparation for the treatment of skin diseases which consists of an effective amount of a steroid in admixture with an adhesive gel base consisting essentially of a water-soluble high molecular weight compound, water, and a water-retaining agent, wherein said water-soluble high molecular weight compound is carboxymethylcellulose, methyl cellulose, polyvinyl alcohol, polyacrylic acid, therapeutically effective metal salts thereof, or a combination or two or more thereof, which is contained in an amount of 0.1 to 30 w/w % in the adhesive gel base, said water-retaining agent being a polyhydric alcohol selected from the group consisting of glycerol, sorbitol, propylene glycol and 1,3-butanediol, which is contained in an amount of 5 to 60 w/w % in an adhesive gel base, or said water-retaining agent having a highly absorptive high molecular weight compound selected from the group consisting of starch - acrylonitrile graft copolymer, starch-acrylic acid graft copolymer, cross-linked product of polyvinyl alcohol, cross-linked product of carboxymethylcellulose, and cross-linked product of polyacrylate, which is contained in an amount of 0.01 to 10.0 w/w % in the adhesive gel base, and said water being contained in an amount of 20 to 50 w/w % in the adhesive gel base.

2. The adhesive preparation as claimed in claim 1, wherein the amount of the water-soluble high molecular weight compound is in the range of from 0.5 to 15 w/w % of the total preparation.

3. The adhesive preparation as claimed in claim 1, wherein the polyhydric alcohol as the water-retaining agent is contained in an amount of from 10 to 50 w/w % of the total preparation.

4. The adhesive preparation as claimed in claim 1, wherein the highly absorptive high molecular weight compound as the water-retaining agent is contained in an amount of from 0.05 to 7.0 w/w % of the total preparation.

5. The adhesive preparation as claimed in claim 1, wherein the steroid is contained in an amount of from 0.01 to 1 w/w % of the total preparation.

6. The adhesive preparation as claimed in claim 1, wherein the adhesive gel base further contains an additive which is an oil, a surfactant, a stabilizing agent, an antioxidant, a pH controlling agent or an organic filler.

7. The adhesive preparation according to claim 1, wherein the adhesive gel base consists of 0.5 to 15 w/w % of the total preparation of a water-soluble high molecular weight compound being a combination of gelatin, carboxymethylcellulose and carboxymethylcellulose sodium salt, 20 to 50 w/w % of water, and 10 to 50 w/w % of a water-retaining agent being a combination of glycerol and sorbitol.

* * * * *

UNITED STATES PATENT AND TRADEMARK OFFICE
CERTIFICATE OF CORRECTION

PATENT NO. : 5,082,663

DATED : January 21, 1992

INVENTOR(S) : Ryoji Konishi, Akihito Oji, Toshikuni Kawaji, Osami Makaya, Manabu Ishihara and Akira Iwasa It is certified that error appears in the above-identified patent and that said Letters Patent is hereby corrected as shown below:

On the Tittle Page:

left column, please change

"[22] PCT Filed: Aug. 20, 1987" to -- [22] Filed: Jan. 11, 1991--

Please delete totally items

" [86] " and " [87] "

Signed and Sealed this

Twelfth Day of July, 1994

*Attest:*

BRUCE LEHMAN

*Attesting Officer*     *Commissioner of Patents and Trademarks*